United States Patent
Aoyagi et al.

(10) Patent No.: US 7,190,453 B1
(45) Date of Patent: Mar. 13, 2007

(54) FILM MEASUREMENT

(75) Inventors: Paul Aoyagi, Sunnyvale, CA (US); Philip D. Flanner, III, Union City, CA (US); Leonid Poslavsky, Belmont, CA (US)

(73) Assignee: KLA-Tencor Technologies Corporation, Milpita, CA (US)

( * ) Notice: Subject to any disclaimer, the term of this patent is extended or adjusted under 35 U.S.C. 154(b) by 347 days.

(21) Appl. No.: 10/945,167

(22) Filed: Sep. 20, 2004

(51) Int. Cl.
*G01J 4/00* (2006.01)
*G01B 11/28* (2006.01)

(52) U.S. Cl. ...................................... 356/369; 356/630

(58) Field of Classification Search ................ 356/369, 356/128, 600, 630
See application file for complete search history.

(56) References Cited

U.S. PATENT DOCUMENTS

| | | | | |
|---|---|---|---|---|
| 4,999,014 A | * | 3/1991 | Gold et al. ................. | 356/632 |
| 5,121,337 A | * | 6/1992 | Brown ........................ | 702/28 |
| 6,782,337 B2 | * | 8/2004 | Wack et al. ................ | 702/155 |

OTHER PUBLICATIONS

Li, *Formulation and Comparison of Two Recursive Matrix Algorithms for Modeling Layered Diffraction Grating*, J. Opt. Soc. Am., vol. 13, No. 5, pp. 1024-1035 (1996).

Moharam et al., *Formulation for Stable and Efficient Implementation of the Rigorous Coupled-Wave Analysis of Binary Gratings*, J. Opt. Soc. Am., vol. 12, No. 5, pp. 1068-1076 (1995).

* cited by examiner

*Primary Examiner*—Hwa (Andrew) Lee
*Assistant Examiner*—Roy M. Punnoose
(74) *Attorney, Agent, or Firm*—Luedeka, Neely & Graham, P.C.

(57) ABSTRACT

A method of determining the actual properties of a film stack. An incident beam of light is directed towards the film stack, such that the incident beam of light is reflected from the film stack as a reflected beam of light. The actual properties of the reflected beam of light are measured, and properties of the film stack are estimated. A mathematical model of the film stack is solved with the estimated properties of the film stack to yield theoretical properties of the reflected beam of light. The theoretical properties of the reflected beam of light are compared to the actual properties of the reflected beam of light to yield a cost function. The estimated properties of the film stack are iteratively adjusted and the mathematical model is iteratively solved until the cost function is within a desired tolerance. The estimated properties of the film stack are reported as the actual properties of the film stack. A method based on analytical derivatives, and not numerically computed derivatives, of solutions to Maxwell's equations that are at least partially expressible as complex exponential matrices is used to iteratively adjust the estimated properties of the film stack.

20 Claims, 1 Drawing Sheet

FILM MEASUREMENT

FIELD

This invention relates to the field of film measurement. More particularly, this invention relates to a system for improving the speed and accuracy of multi layered film stack thickness measurement and other property measurement, such as in the integrated circuit fabrication industry.

BACKGROUND

As used herein, the term "integrated circuits" generally refers to monolithic semiconducting devices, such as those formed of group IV materials like silicon or germanium or mixtures thereof, or group III–V compounds such as gallium arsenide. The term "integrated circuits" includes all known configurations of such devices, such as memory and logic, and all designs of such devices, such as CMOS and bipolar.

Integrated circuits are formed of many layers of different materials, which layers are patterned so as to form desired structures that interact with one another according to predetermined designs. Thus, it is of vital importance that many of these layers be formed to very exacting tolerances, such as in their shape, thickness, and composition. If the various structures so formed during the integrated circuit fabrication process are not precisely formed, then the integrated circuit tends to not function in the intended manner, and may not function at all.

Because the layers of which integrated circuits are formed are so thin and patterned to be so small, they cannot be inspected without the aid of instrumentation. The precision of the instrumentation used is, therefore, vital to the successful production of integrated circuits. Thus, any improvement that can be made in the accuracy of such instrumentation is a boon to the integrated circuit fabrication industry. In addition, any improvement in the speed at which such instrumentation can take its readings is also of benefit to the industry, as such speed enhancements tend to reduce the production bottlenecks at inspection steps, or alternately allow for the inspection of a greater number of integrated circuits at such inspection steps.

Spectral ellipsometers and dual beam spectrophotometers are typically used to measure properties such as thickness and refractive index of individual layers within a multilayered film stack. Such instruments work by directing one or more beams of light toward the surface of the film stack, and then sensing the properties of the light as it is variously reflected off of the different surfaces of the individual layers within the film stack. By adjusting the properties of the incident beam of light, and detecting the associated changes in the reflected beam of light, the properties of the film stack, such as the materials of which the various layers are formed and thicknesses to which they are formed, can be determined.

This film measurement process can be broken down into two basic steps, being 1) the measurement of the properties of the reflected light beam, and 2) the mathematical fitting of computed reflectance property values based on some theoretical model, such as Rigorous Coupled Wave Analysis, to the measured results attained in step 1. Step 2 typically consists of the iterated steps of computing one or more theoretical value by plugging estimates of the film stack parameters, such as thickness and refractive index, into the model film stack equations, comparing the theoretical values obtained to the actual measured property values of the reflected beam of light, and if the theoretical values and the measured values do not agree to within a desired tolerance, then adjusting the estimated film stack parameters and recomputing the theoretical values.

This process is performed again and again, each time making some adjustment to the estimated film stack parameters that are fed into the model, until the theoretical values computed by the model agree with the actual measured values within the desired precision limits. When this agreement is attained, then there is some confidence that the estimated film stack parameters that were used to produce the theoretical values are very nearly the same as the actual film stack parameters.

For many film stacks, the step of iterative computing as described above consumes by far the most time during the process. For some film stacks, such as those film stacks that contain patterned lines, this iterative steps become extremely complex, because of the tremendous overhead of computing and tracking reflections at multiple diffracting angles. Currently, the theoretical reflectance values are determined using numerical derivatives for the reflectance, because exact, closed-form expressions for these derivatives has heretofore not been found.

Unfortunately, the current methods tend to suffer from several problems. First, the extra mathematical computations that are required by the numerical methods tends to limit the speed at which measurements can be taken, thus reducing the throughput of the instrument. Second, such numerical methods tend to have a reduced degree of accuracy resulting in decreased robustness and reliability.

What is needed, therefore, is a method of spectral film stack measurement that tends to reduce at least some of the problems described above.

SUMMARY

The above and other needs are met by a method of determining the actual properties of a film stack. An incident beam of light is directed towards the film stack, such that the incident beam of light is reflected from the film stack as a reflected beam of light. The actual properties of the reflected beam of light are measured, and properties of the film stack are estimated. A mathematical model of the film stack is solved with the estimated properties of the film stack to yield theoretical properties of the reflected beam of light. The theoretical properties of the reflected beam of light are compared to the actual properties of the reflected beam of light to yield a cost function. The estimated properties of the film stack are iteratively adjusted and the mathematical model is iteratively solved until the cost function is within a desired tolerance. The estimated properties of the film stack are reported as the actual properties of the film stack. A method based on analytical derivatives, and not numerically computed derivatives, of solutions to Maxwell's equations that are at least partially expressible as complex exponential matrices is used to iteratively adjust the estimated properties of the film stack.

Thus, the present invention defines over the prior art in that an analytical method is used to determine the solutions to the mathematical model of the film stack, instead of relying on less accurate and more time consuming numerical methods. In particular, for models of inhomogeneous film stacks that are at least partially expressible as non-diagonal complex exponential matrix solutions to Maxwell's equation, such a solution was previously thought to be intractable or impossible. However, a method has been discovered by the present inventors to manipulate the equations for this case in a manner where they can be solved analytically. That method is described herein.

In various embodiments, the method is implemented in an ellipsometer. The film stack may include layers of more than one material, and more than one layer. The film stack preferably includes a patterned layer. The actual properties of the film stack preferably include at least one of layer thickness and layer refractive index. Preferably, the mathematical model is computationally solved using matrix operations. Most preferably, the mathematical model is a reflectance model that is derived at least in part from rigorous coupled wave analysis. The estimated properties of the film stack are preferably derived exactly and in closed form. The equation to be used iteratively estimating properties of the film stack based on reflectance is preferably given by:

$$\frac{\partial \chi^2}{\partial P_n} \approx \sum_{m=0}^{M} -2\left(\frac{R_{meas}(\lambda_m) - R'_{theory}(P_0, P_1 \ldots P_N)}{\sigma_m}\right)\frac{\partial R_{theory}}{\partial P_n} = 0.$$

A generalized expression of the above is given by:

$$\frac{\partial C(R_{meas}(\lambda_m), R_{theory}(\lambda_m, P))}{\partial P_n} = \sum_{m=0}^{M} \left(\frac{\partial C}{\partial R_{theory}}\right)\left(\frac{\partial R_{theory}(\lambda_m, P)}{\partial P_n}\right) = 0$$

where C is the cost function, $R_{theory}$ is the theoretical reflectance, $R_{meas}$ is the measured reflectance, $P_n$ is a variable of the theoretical reflectance model (i.e. film stack parameters), $\lambda_m$ is the $m^{th}$ wavelength, m is the integer index, M is the total number of wavelength values, and $\sigma_m$ is the measurement uncertainty at $\lambda_m$.

The preferred embodiments of the present invention differ from prior art methods in that the reflectance derivatives from with respect to the parameters of the film stack, including without limitation pitch, critical dimension, and refractive index, needed for regression are done exactly and in a closed form. An operation count of numerical derivatives based on a three-point central difference approximation and the analytic derivatives shows that this method reduces the number of full matrix multiplications by a factor of up to about four, depending on the amount of caching that is made available. Moreover, this method greatly improves the robustness, speed, and reliability of the measurement, because it eliminates the numerical errors and potential convergence problems associated with using numerical derivatives.

Relative to the methods that use numerical derivatives, it is believed that the preferred embodiments of the invention reduce the computation time needed for measurement by approximately 15% to 40%. The reduction can be significantly greater in those cases where the numerical derivatives do not converge. Many of the current methods of measuring films containing patterned metal are based on rigorous coupled wave analysis. Consequently, the preferred embodiments of the present invention provide an immediate low-cost advantage with respect to the reliable, accurate, and fast real-time measurement of multi-layered film stacks containing patterned lines.

This invention is preferably implemented as an add-in to existing instrument software.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Ellipsometry methods generally begin by computing the cost or error function, for example:

$$C(R_{meas}(\lambda), R_{theory}(\lambda, P)) \qquad 1$$

Where $R_{meas}$ is a function of wavelength ($\lambda$), and $R_{theory}$ is a multivariable function in $\lambda$ and P, and where:

$$P = (P_0, P_1, P_2, \ldots P_N).$$

Minimize equation 1 with respect to P. There are two ways to do this. One method requires derivatives and the other does not. In general, methods that require derivatives converge faster than those that do not use derivatives and are, for that reason, preferable. The derivative approach requires finding values that make the first derivatives equal to zero, for example, $$\frac{\partial C}{\partial P_n} = \sum_{m=0}^{M} \left(\frac{\partial C}{\partial R_{theory}}\right)\left(\frac{\partial R_{theory}}{\partial P_n}\right) = 0 \qquad 2$$

Where:

n=0, 1, . . . N.

Equation 2 is N equations in N unknowns, because there are N derivatives corresponding to N parameters which must be set to zero. To solve equation 2 using linear algebra theory, it is generally necessary to approximate $R_{theory}$ with its linear approximation $R'_{theory}$ using a Taylor series expansion, for example, $$R_{theory}(P) \approx R'_{theory}(P) = R_{theory}(P_o) + \sum_{n=0}^{N} \left.\frac{\partial R_{theory}}{\partial P_n}\right|_{P=P_o} (P_n - P_{no}) \qquad 3$$

Where:

P=($P_{00}$, $P_{10}$ . . . $P_{N0}$).

As alluded to above, one novel aspect of the various embodiments according to the present invention lies in the regression algorithm and, in particular, the derivatives used therein. $R_{theory}$ derivatives in equations 2 and 3 can be computed numerically or analytically. Preferably, these derivatives are computed analytically so as to not only improve the accuracy of the method, but also to remove the nonconvergence problems that are associated with numerical derivatives. Moreover, analytical derivatives tend to be more amenable to computational efficiency improvements associated with the caching of intermediate variables. Thus, embodiments of the present invention tend to be both faster than numerical methods and more accurate than numerical methods.

In practice, analytical derivatives are not always derivable due to the mathematical complexity of $R_{theory}$. An important case in point is the $R_{theory}$ derivatives based on the Rigorous Coupled Wave Analysis. The Rigorous Coupled Wave Analysis model is one of the most if not the most widely used physical model used in ellipsometry and scatterometry measurements over patterned inhomogeneous media. The expressions for the derivatives of $R_{theory}$, however, are not readily computed because of the numerical eigenvalue/eigenvector computations involved. One of the novelties in the various embodiments according to the present invention is that analytic expressions for $R_{theory}$ derivatives are derived based on the Rigorous Coupled Wave Analysis. A generalized expression of the equation is given by:

$$\frac{\partial C(R_{meas}(\lambda_m), R_{theory}(\lambda_m, P))}{\partial P_n} = \sum_{m=0}^{M} \left(\frac{\partial C}{\partial R_{theory}}\right)\left(\frac{\partial R_{theory}(\lambda_m, P)}{\partial P_n}\right) = 0 \qquad 4$$

where C is the cost function, $R_{theory}$ is the theoretical reflectance, $R_{meas}$ is the measured reflectance, $P_n$ is a variable of the theoretical reflectance model (i.e. film stack parameters), $\lambda_m$ is the $m^{th}$ wavelength, m is the integer index, M is the total number of wavelength values, and $\sigma_m$ is the measurement uncertainty at $\lambda_m$.

Figure 1:
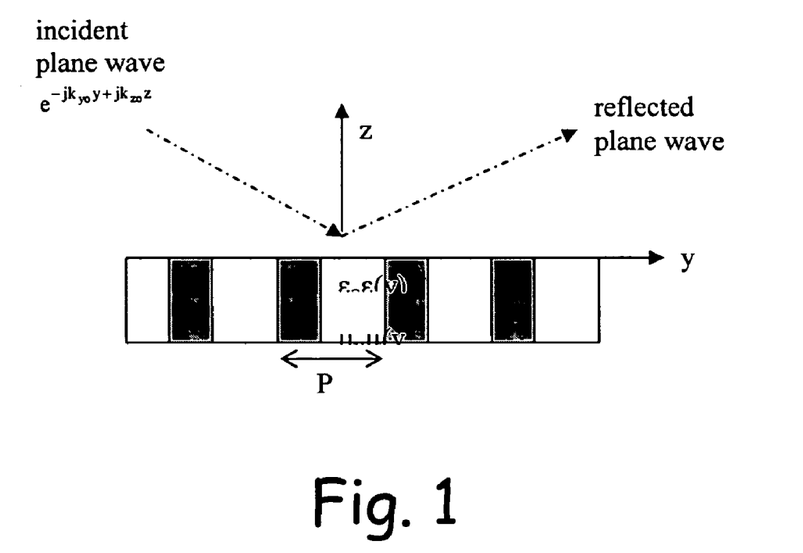
FIG. 1 is a representation of a plane wave incident on a grating structure.

The first step in the process to produce this analytic expression is to derive governing partial differential equations for a TE (E field parallel to the grating grooves) and TM plane (E field perpendicular to the grating grooves) wave incident on the planar grating shown in FIG. 1. It is noted that the discussions provided herein assume that the reader is generally familiar with the art of ellipsometry, and thus most terms are not specifically defined herein. However, the basic equations, variables, and methods are known to those with skill in the art.

RIGOROUS COUPLED WAVE ANALYSIS FORMULATION

The TE case is defined by $(E_x, H_y, H_z) \neq 0$, and where all other field components are zero. E and H are the electric and magnetic fields, respectively, and is preferably solved using Maxwell's equations. For the TE case the equations simplify to:

$$j\omega\varepsilon_o\varepsilon(y)E_x = \frac{\partial H_z}{\partial y} - \frac{\partial H_y}{\partial z} \qquad 5$$

$$-j\omega\mu_o\mu(y)H_y = \frac{\partial E_x}{\partial z}; \; j\omega\mu_o\mu_z(y)k_o^2 H_z = \frac{\partial E_x}{\partial y} \qquad 6$$

Where $\epsilon$=relative dielectric permittivity, $\mu$=relative magnetic permeability in the (x, y) direction, $\mu_z$=relative magnetic permeability in the z direction, and $\epsilon_0$ and $\mu_0$=dielectric permittivity and magnetic permeability of free space, respectively.

Because the grating structure is periodic in the y axis, the electromagnetic fields and the grating profile is preferably expresses as a Fourier series, for example:

$$E_x = \sum_{n=-N}^{N} e_{x,n}(x,z) e^{j\left(\frac{2\pi n}{P} - k_{yo}\right)y} \qquad 7$$

$$H_y = \sum_{n=-N}^{N} h_{y,n}(x,z) e^{j\left(\frac{2\pi n}{P} - k_{yo}\right)y}; \; H_z = \sum_{n=-N}^{N} h_{z,n}(x,z) e^{j\left(\frac{2\pi n}{P} - k_{yo}\right)y} \qquad 8$$

-continued $$\varepsilon = \sum_{n=-N}^{N} \varepsilon_n e^{-j\frac{2\pi n}{P}y}; \; \mu = \sum_{n=-N}^{N} \mu_n e^{-j\frac{2\pi n}{P}y}, \; \mu_z = \sum_{n=-N}^{N} \mu_{z,n} e^{-j\frac{2\pi n}{P}y} \qquad 9$$

From orthogonality, each Fourier harmonic preferably independently satisfies Maxwell's equations. Therefore, Maxwell's equations are preferably expressed in the following matrix form:

$$j\omega\varepsilon_o E e_x = \frac{\partial h_z}{\partial y} - \frac{\partial h_y}{\partial z} \qquad 10$$

$$-j\omega\mu_o M h_y = \frac{\partial e_x}{\partial z}; \; j\omega\mu_o k_o^2 M_z h_z = \frac{\partial e_x}{\partial y} \qquad 11$$

Where:

$$e_x = \begin{bmatrix} e_{x,-N} \\ e_{x,-(N-1)} \\ \vdots \\ e_{x,o} \\ \vdots \\ e_{x,(N-1)} \\ e_{x,N} \end{bmatrix} \; h_y = \begin{bmatrix} h_{y,-N} \\ h_{y,-(N-1)} \\ \vdots \\ h_{y,o} \\ \vdots \\ h_{y,(N-1)} \\ h_{y,N} \end{bmatrix} \; h_z = \begin{bmatrix} h_{z,-N} \\ h_{z,-(N-1)} \\ \vdots \\ h_{z,o} \\ \vdots \\ h_{z,(N-1)} \\ h_{z,N} \end{bmatrix} \qquad 12$$

and $$E = \begin{bmatrix} \varepsilon_0 & \varepsilon_1 & \cdots & \varepsilon_{-N} \\ \varepsilon_1 & \varepsilon_0 & \cdots & \varepsilon_{-(N-1)} \\ \vdots & \cdots & \cdots & \vdots \\ \varepsilon_N & \varepsilon_{N-1} & \cdots & \varepsilon_0 \end{bmatrix}, \; M = \begin{bmatrix} \mu_0 & \mu_1 & \cdots & \mu_{-N} \\ \mu_1 & \mu_0 & \cdots & \mu_{-(N-)} \\ \vdots & \vdots & \cdots & \vdots \\ \mu_N & \mu_{N-1} & \cdots & \mu_0 \end{bmatrix},$$

$$M_z \begin{bmatrix} \mu_{z,0} & \mu_{z,1} & \cdots & \mu_{z,-N} \\ \mu_{z,1} & \mu_0 & \cdots & \mu_{z,-(N-1)} \\ \vdots & \vdots & \cdots & \vdots \\ \mu_{z,N} & \mu_{z,N-1} & \cdots & \mu_{z,0} \end{bmatrix} \qquad 13$$

Equation 11 is preferably alternately written as:

$$-j\omega\mu_o h_y = A_\mu \frac{\partial e_x}{\partial z}; \; j\omega\mu_o h_z = A_{\mu_z} \frac{\partial e_x}{\partial y} \qquad 14$$

Where:

$$A_\mu = \begin{bmatrix} a_0 & a_1 & \cdots & a_{-N} \\ a_1 & a_0 & \cdots & a_{-(N-1)} \\ \vdots & \vdots & \cdots & \vdots \\ a_N & a_{N-1} & \cdots & a_o \end{bmatrix}, \; A_{\mu_z} = \begin{bmatrix} a_{z,0} & a_{z,1} & \cdots & a_{z,-N} \\ a_{z,1} & a_{z,0} & \cdots & a_{z,-(N-1)} \\ \vdots & \vdots & \cdots & \vdots \\ a_{z,N} & a_{z,N-1} & \cdots & a_{z,o} \end{bmatrix}$$

and $$\frac{1}{\mu} = \sum_{n=-N}^{N} a_n e^{-j\frac{2\pi n}{p}y} \frac{1}{\mu_z} = \sum_{n=-N}^{N} a_{z,n} e^{-j\frac{2\pi n}{p}y}$$

Equations 11 and 14 are self-consistent with respect to their usage of M or $A_\mu$. For the present purposes, the following hybrid is preferably used:

$$h_y = \left(\frac{1}{-j\omega\mu_o}\right) A_\mu \frac{\partial e_x}{\partial z}; h_z = \left(\frac{1}{j\omega\mu_o}\right) M_z^{-1} \frac{\partial e_x}{\partial y} \qquad 15$$

In general, equation 15 is not self-consistent, since $M^{-1} \neq A_\mu$. However, equation 15 is preferably used in the present method, because it has been determined to have more rapid convergence of the field solutions as the number of field harmonics is increased. Combining equations 5 and 15 yields:

$$-A_\mu^{-1}\left[-\frac{\partial}{\partial y}\left(M_z^{-1}\frac{\partial}{\partial y}\right) - E\right] e_x = -\frac{1}{k_o^2}\frac{\partial^2 e_x}{\partial z^2} \qquad 16$$

Note that $$\frac{\partial}{\partial y} \to jk_{ym},$$

where the m subscript denotes the $m^{th}$ harmonic.

$$-S^2 e_x = A_\mu^{-1}[K_y M_z^{-1} K_y - E]e_x = \frac{1}{k_o^2}\frac{\partial^2 e_x}{\partial z^2} \qquad 17$$

For isotropic magnetic permeability, $M^{-1} = M_z^{-1} = A_\mu = I$. Therefore, the TE case is preferably given by:

$$-S^2 e_x = [K_y^2 - E]e_x = \frac{1}{k_o^2}\frac{\partial^2 e_x}{\partial z^2} \qquad 18$$

The TM case is defined by $(H_x, E_y, E_z) \neq 0$, and where all other field components are zero. The TM case equations are preferably obtained from the TE case equations by duality. Equation 17 thereby yields:

$$-S^2 h_x = A_\varepsilon^{-1}[K_y E_z^{-1} K_y - M]h_x = \frac{1}{k_o^2}\frac{\partial^2 h_x}{\partial z^2} \qquad 19$$

For isotropic magnetic permeability, $M = A_\mu = I$. Therefore, the TM case is preferably given by:

$$-S^2 h_x = A_\varepsilon^{-1}[K_y E_z^{-1} K_y - I]h_x = \frac{1}{k_o^2}\frac{\partial^2 h_x}{\partial z^2} \qquad 20$$

Both the TE and the TM differential equations as derived above are preferably summarized as:

$$-S^2 f = \frac{1}{k_o^2}\frac{\partial^2 f}{\partial z^2}: f = \begin{cases} TE: e_x \\ TM: h_x \end{cases} : -S^2 = \begin{cases} TE: A_\mu^{-1}[K_y M_z^{-1} K_y - E] \\ TM: A_\varepsilon^{-1}[K_y E_z^{-1} K_y - M] \end{cases} \qquad 21$$

By inspection, the complex exponential matrix functions given by $e^{\pm jk_oSz}$ are solutions to 21, therefore:

$$f = e^{jk_oSz}d_+ + e^{-jk_oSz}d_- \qquad 22$$

Where $d_\pm$ are arbitrary column vector constants.

Using DeMoivre's identity, equation 22 can alternately be expressed as:

$$f = \cos(k_oSz)d_+ + \sin(k_oSz)d_-$$

Equation 22 can also be alternately expressed as:

$$f = W^{-1}e^{jk_oK_zz}Wd_+ + W^{-1}e^{-jk_oK_zz}Wd_-$$

where W = eigenvector matrix and $K_z$ = eigenvalue (diagonal) matrix such that $S^2 = WK_z^2W^{-1}$

A REFLECTANCE UPDATE FORMULATION

Figure 2:
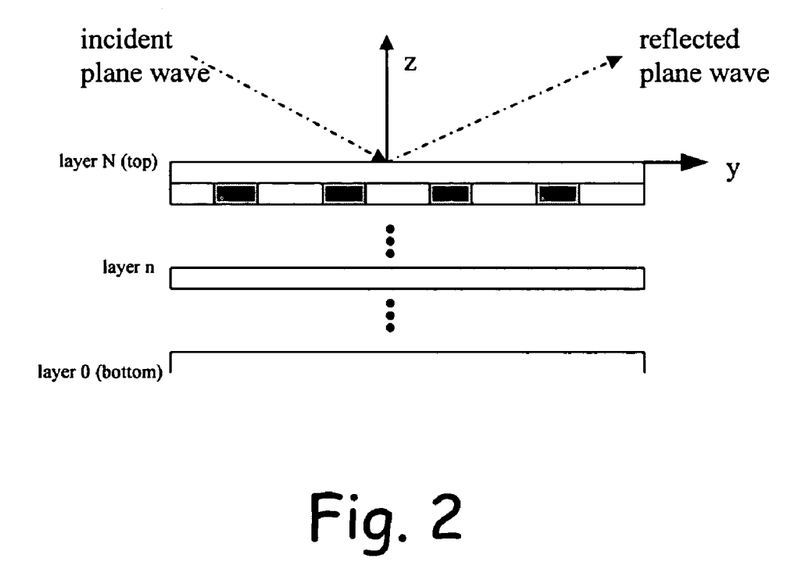
FIG. 2 is a representation of an N-layer film stack with multiple grating layers.

The next step in the method is preferably to develop a method to compute the TE and TM reflectance of an N-layer film stack containing multiple gratings, as depicted in FIG. 2.

For the purposes of example, the detailed analysis for only the TE case is presented. Analogous results for the TM case can be derived from the TE case, using the same duality principle applied earlier in 19. The first step for the TE case is preferably to consider the electromagnetic fields, i.e., the solution to Maxwell's equations, in the form given by 22:

$$e_x = e^{jk_oSz}d_+ + e^{-jk_oSz}d_- \qquad 23$$

$$h_{y'} = -h_y = A_\mu S(e^{jk_oSz}d_+ - e^{-jk_oSz}d_-) \qquad 24$$

$$\begin{bmatrix} e_x \\ h_{y'} \end{bmatrix} = \begin{bmatrix} I & I \\ A_\mu S & -A_\mu S \end{bmatrix} \begin{bmatrix} e^{jk_oSz} & 0 \\ 0 & e^{-jk_oSz} \end{bmatrix} \begin{bmatrix} d_+ \\ d_- \end{bmatrix} \qquad 25$$

The next step is preferably to find $c_\pm$ in terms of tangential fields at z=0, for example, $e_{xo}$, $h_{y'o}$, as next given:

$$d_+ + d_- = e_{xo} \qquad 26$$

$$d_+ - d_- = S^{-1}A_\mu^{-1}h_{y'o} \qquad 27$$

$$d_\pm = \frac{1}{2}(e_{xo} \pm S^{-1}A_\mu^{-1}h_{y'o}) \qquad 28$$

$$\begin{bmatrix} d_+ \\ d_- \end{bmatrix} = \frac{1}{2}\begin{bmatrix} I & S^{-1}A_\mu^{-1} \\ I & -S^{-1}A_\mu^{-1} \end{bmatrix}\begin{bmatrix} e_{xo} \\ h_{y'o} \end{bmatrix} = \frac{1}{2}\begin{bmatrix} I & (A_\mu S)^{-1} \\ I & -(A_\mu S)^{-1} \end{bmatrix}\begin{bmatrix} e_{xo} \\ h_{y'o} \end{bmatrix} \qquad 29$$

$$\begin{bmatrix} e_x \\ h_{y'} \end{bmatrix} = \frac{1}{2}G\begin{bmatrix} e_{xo} \\ h_{y'o} \end{bmatrix} = \qquad 30$$

$$\frac{1}{2}\begin{bmatrix} I & I \\ (A_\mu S) & -(A_\mu S) \end{bmatrix}\begin{bmatrix} e^{jk_oSz} & 0 \\ 0 & e^{-jk_oSz} \end{bmatrix}\begin{bmatrix} I & (A_\mu S)^{-1} \\ I & -(A_\mu S)^{-1} \end{bmatrix}\begin{bmatrix} e_{xo} \\ h_{y'o} \end{bmatrix}$$

An impedance $Z_n$ is preferably defined, which relates the tangential magnetic field to the tangential electric field at the top of the nth layer, for example:

$$\begin{bmatrix} Z_n h_{y',n} \\ h_{y',n} \end{bmatrix} = \begin{bmatrix} e_{x,n} \\ h_{y',n} \end{bmatrix} \quad (31)$$

Equation 30 is preferably rewritten as:

$$\begin{bmatrix} Z_n h_{y',n} \\ h_{y',n} \end{bmatrix} = \frac{1}{2}\begin{bmatrix} I & I \\ V_n & -V_n \end{bmatrix}\begin{bmatrix} e^{jk_o S_n z} & 0 \\ 0 & e^{-jk_o S_n z} \end{bmatrix}\begin{bmatrix} I & V_n^{-1} \\ I & -V_n^{-1} \end{bmatrix}\begin{bmatrix} Z_{n-1} h_{y',n-1} \\ h_{y',n-1} \end{bmatrix} \quad (32)$$

Where $$V_n = A_{\mu,n} S_n.$$

At this point there is preferably defined a value $R'_{b,n}$ as given below:

$$\begin{bmatrix} e'_{b,n} \\ R'_{b,n} e'_{b,n} \end{bmatrix} = \begin{bmatrix} I & V_n^{-1} \\ I & -V_n^{-1} \end{bmatrix}\begin{bmatrix} Z_{n-1} h_{y',n-1} \\ h_{y',n-1} \end{bmatrix} \Rightarrow R'_{b,n} = (Z_{n-1} - V_n^{-1})(Z_{n-1} + V_n^{-1})^{-1} \quad (33)$$

Equation 23 is then preferably rewritten as:

$$R'_{b,n} = (Z_{n-1} - V_n^{-1})(Z_{n-1} + V_n^{-1})^{-1} = W_n R_{b,n} W_n^{-1} \quad (34)$$

Where $$R_{b,n} = (D_{0,n} - O_n^{-1})(D_{0,n} + O_n^{-1})^{-1} \quad (35)$$

$$D_{0,n} = W_n^{-1} Z_{n-1} \quad (36)$$

$$O_n = A_{\mu,n} W_n K_{z,n} = V_n W_n \quad (37)$$

There is then preferably defined a value $R'_{t,n}$ as given below:

$$\begin{bmatrix} e'_{t,n} \\ R'_{t,n} e'_{t,n} \end{bmatrix} = \begin{bmatrix} e^{jk_o S_n z} & 0 \\ 0 & e^{-jk_o S_n z} \end{bmatrix}\begin{bmatrix} e'_{b,n} \\ R'_{b,n} e'_{b,n} \end{bmatrix} \Rightarrow R'_{t,n} = e^{-jk_o S_n z} R'_{b,n} e^{-jk_o S_n z} \quad (38)$$

or equivalently, $$R'_{t,n} = e^{-jk_o S_n z} R'_{b,n} e^{-jk_o S_n z} = W_n e^{-jk_o K_{z,n} z} R_{b,n} e^{-jk_o K_{z,n} z} W_n^{-1} = W_n R_{t,n} W_n^{-1} \quad (39)$$

Where:

$$R_{t,n} = e^{-jk_o K_{z,n} z} R_{b,n} e^{-jk_o K_{z,n} z} \quad (40)$$

Substituting equation 38 into equation 32 yields:

$$\begin{bmatrix} Z_n h_{y',n} \\ h_{y',n} \end{bmatrix} = \frac{1}{2}\begin{bmatrix} I & I \\ V_n & -V_n \end{bmatrix}\begin{bmatrix} e'_{t,n} \\ R'_{t,n} e'_{t,n} \end{bmatrix} \quad (41)$$

Equation 41 then implies:

$$Z_n = (I + R'_{t,n})[V_n(I - R'_{t,n})]^{-1} \quad (42)$$

With substitution into equation 39 then yielding:

$$Z_n = W_n Z'_n O_n^{-1} \quad (43)$$

Where:

$$Z'_n = (I + R_{t,n})(I - R_{t,n})^{-1} \quad (44)$$

RIGOROUS COUPLED WAVE ANALYSIS GRATING LAYER DERIVATIVE FORMULATION

The next step of the method is preferably to derive equations to analytically compute the derivatives of the reflectance coefficient, for example $R_{b,N}$, in isotropic space at the top of an N-layer film stack with respect to the parameters of a grating layer, as depicted in FIG. 2.

The derivative computation is preferably assumed to consist of three steps, for example:

1. Computation of the impedance derivative at the grating layer, i.e., $\partial Z_n$ computation.
2. Computation of the derivative of the impedance matrix at $N-1$ using iteration, i.e., $\partial Z_{N-1} = f_d(f_d(\ldots f_d(\partial Z_n) \ldots))$ where $f_d(\ )$ is a function which relates $\partial Z_n$ to $\partial Z_{n+1}$ for $0 < n < N$.
3. Computation of $\partial R_{b,N}$ from $\partial Z_{N-1}$ The computations associated with these three steps are given in order below.

IMPEDANCE DERIVATIVE AT THE GRATING LAYER: $\partial Z_n$ COMPUTATION

First, there is preferably derived an expression for $\partial Z_n$, when the parameter over which the derivative taken is in the $n^{th}$ layer. This preferably starts with the impedance equations 42, 43, 39, 34, and 35 respectively, as given below:

$$Z_n = (I + R'_{t,n})[V_n(I - R'_{t,n})]^{-1} = W_n Z'_n O_n^{-1} \quad (45)$$

$$R'_{t,n} = e^{-jk_o S_n z} R'_{b,n} e^{-jk_o S_n z} = W_n e^{-jk_o K_{z,n} z} W_n^{-1} R'_{b,n} W_n e^{-jk_o K_{z,n} z} W_n^{-1} \quad (46)$$

$$R'_{b,n} = (Z_{n-1} - V_n^{-1})(Z_{n-1} + V_n^{-1})^{-1} = W_n(D_n - O_n^{-1})(D_n + O_n^{-1})^{-1} W_n^{-1} = W_n R_{b,n} W_n^{-1} \quad (47)$$

Where:

$$D_n = W_n^{-1} Z_{n-1} \quad (48)$$

$$V_n = A_{\mu,n} S_n = O_n W_n^{-1} \quad (49)$$

Equation 46 is preferably rewritten as:

$$R'_{t,n} = e^{-jk_o S_n z} R'_{b,n} e^{-jk_o S_n z} = W_n e^{-jk_o K_{z,n} z} R_{b,n} e^{-jk_o K_{z,n} z} W_n^{-1} = W_n R_{t,n} W_n^{-1} \quad (50)$$

It is noted that equation 1 is used instead of the expression $Z_n = W_n(I + R_{t,n})(I - R_{t,n})^{-1} O_n^{-1}$, because preferably only analytical expressions are used for the derivatives of $e^{-jk_o S_n z}$ and $V_n$.

Therefore, $$\partial Z_n = \partial R'_{t,n}[V_n(I - R'_{t,n})]^{-1} - (I + R'_{t,n})[V_n(I - R'_{t,n})]^{-1} \partial [V_n(I - R'_{t,n})][V_n(I - R'_{t,n})]^{-1} \quad (51)$$

$$\partial Z_n(\partial R'_{t,n} - Z_n \partial [V_n(I - R'_{t,n})])[V_n(I - R'_{t,n})]^{-1} \quad (52)$$

Expanding the expression $\partial[V_n(I - R'_{t,n})]$ yields:

$$\partial Z_n = (\partial R'_{t,n} - Z_n[\partial V_n(I - R'_{t,n}) - V_n \partial R'_{t,n}])[V_n(I - R'_{t,n})]^{-1} \quad (53)$$

$$\partial Z_n = (\partial R'_{t,n} + Z_n V_n \partial R'_{t,n} - Z_n \partial V_n(I - R'_{t,n}))[V_n(I - R'_{t,n})]^{-1} \quad (54)$$

Substituting in the expression $V_n = Z_{\mu,n} S_n = O_n W_n^{-1}$ yields:

$$\partial Z_n = (\partial R'_{t,n} + Z_n O_n W_n^{-1} \partial R'_{t,n} - Z_n \partial V_n + Z_n \partial V_n R'_{t,n}) [O_n W_n^{-1}(I - R'_{t,n})]^{-1} \quad (55)$$

Substituting in equation 45 from above, $Z_n = W_n Z'_n O_n^{-1}$ yields: 56

$$\partial Z_n = (\partial R'_{t,n} + W_n Z'_n W_n^{-1} \partial R'_{t,n} - W_n Z'_n O_n^{-1} \partial V_n (I - R'_{t,n}))[W_n^{-1}(I - R'_{t,n})]^{-1} O_n^{-1} \quad (57)$$

Substituting in $R'_{t,n} = W_n R_{t,n} W_n^{-1}$ yields:

$$\partial Z_n = (\partial R'_{t,n} + W_n Z'_n W_n^{-1} \partial R'_{t,n} - W_n Z'_n O_n^{-1} \partial V_n (I - W_n R_{t,n} W_n^{-1}))[W_n^{-1}(I - W_n R_{t,n} W_n^{-1})]^{-1} O_n^{-1} \quad (58)$$

Then by factoring $W_n$ to the left yields:

$$\partial Z_n = W_n(W_n^{-1} \partial R'_{t,n} + Z'_n W_n^{-1} \partial R'_{t,n} - Z'_n O_n^{-1} \partial V_n W_n(I - R_{t,n}) W_n^{-1})[W_n^{-1} W_n(I - R_{t,n}) W_n^{-1}]^{-1} O_n^{-1} \quad (59)$$

$$\partial Z_n = W_n(W_n^{-1} \partial R'_{t,n} + Z'_n W_n^{-1} \partial R'_{t,n} - Z'_n O_n^{-1} \partial V_n W_n(I - R_{t,n}) W_n^{-1}) W_n (I - R_{t,n})^{-1} O_n^{-1} \quad (60)$$

The next step is preferably to multiply through with $W_n$ from the right side, yielding:

$$\partial Z_n = W_n(W_n^{-1} \partial R'_{t,n} W_n + Z'_n W_n^{-1} \partial R'_{t,n} W_n - Z'_n O_n^{-1} \partial V_n W_n (I - R_{t,n}))(I - R_{t,n})^{-1} O_n^{-1} \quad (61)$$

Find $$\partial V_n = \partial A_{\mu,n} S_n + A_{\mu,n} \partial S_n = \partial A_{\mu,n} W_n K_{z,n} W_n^{-1} + A_{\mu,n} \partial S_n \quad (62)$$

Recall $$S_n = W_n K_{z,n} W_n^{-1} \quad (63)$$

$$\partial S_n = W_n X_n W_n^{-1} \quad (64)$$

Where $F_n$ = Fourier series coefficient matrix (frequency independent).

$$X_n = \frac{W_n^{-1} \partial S_n^2 W_n}{K_{s,n}} \text{ where } \left\{ C \equiv \frac{A}{B} : c_{mn} = \frac{a_{mn}}{b_{mn}} \right\} \text{ and } K_{s,n} : k_{sij} = (k_{zi} + k_{zj})$$

Therefore:

$$\partial V_n = \partial A_{\mu,n} W_n K_{z,n} W_n^{-1} + A_{\mu,n} W_n X_n W_n^{-1} \quad (65)$$

Factoring out $O_n$ yields $\partial V_n = O_n(O_n^{-1} \partial A_{\mu,n} W_n K_{z,n} + K_{z,n}^{-1} X_n) W_n^{-1} = O_n \Phi_n W_n^{-1}$ (66)

Substituting equation 66 into equation 61 yields:

$$\partial Z_n = W_n(W_n^{-1} \partial R'_{t,n} W_n + Z'_n W_n^{-1} \partial R'_{t,n} W_n - Z'_n O_n^{-1} \partial V_n W_n (I - R_{t,n}))(I - R_{t,n})^{-1} O_n^{-1} \quad (67)$$

$$\partial Z_n = W_n(W_n^{-1} \partial R'_{t,n} W_n + Z'_n W_n^{-1} \partial R'_{t,n} W_n - Z'_n \Phi_n (I - R_{t,n}))(I - R_{t,n})^{-1} O_n^{-1} \quad (68)$$

Finding $\partial R'_{t,n}$, and recalling from equation 46 that:

$$R'_{t,n} = e^{-jk_o S_n z} R'_{b,n} e^{-jk_o S_n z} \quad (69)$$

Therefore:

$$\partial R'_{t,n} = \partial e^{-jk_o S_n z} R'_{b,n} e^{-jk_o S_n z} + e^{-jk_o S_n z} \partial R'_{b,n} e^{-jk_o S_n z} + e^{-jk_o S_n z} R'_{b,n} \partial e^{-jk_o S_n z} \quad (70)$$

Finding $\partial R'_{b,n}$, and recalling from equation 47 that:

$$R'_{b,n} = (Z_{n-1} - V_n^{-1})(Z_{n-1} + V_n^{-1})^{-1} \quad (71)$$

$$\partial R'_{b,n} = -\partial V_n^{-1}(Z_{n-1} + V_n^{-1})^{-1} - (Z_{n-1} - V_n^{-1})(Z_{n-1} + V_n^{-1})^{-1} \partial V_n^{-1}(Z_{n-1} + V_n^{-1})^{-1} \quad (72)$$

With substitution from equation 47, this yields:

$$\partial R'_{b,n} = -\partial V_n^{-1}(Z_{n-1} + V_n^{-1})^{-1} - R'_{b,n} \partial V_n^{-1}(Z_{n-1} + V_n^{-1})^{-1} \quad (73)$$

Factoring yields:

$$\partial R'_{b,n} = -(I + R'_{b,n}) \partial V_n^{-1}(Z_{n-1} + V_n^{-1})^{-1} = -(I + R'_{b,n}) \partial V_n^{-1} (D_n + O_n^{-1})^{-1} W_n^{-1} \quad (74)$$

Finding $$\partial V_n^{-1} = -V_n^{-1} O_n \Phi_n W_n^{-1} V_n^{-1} = -(W_n O_n^{-1}) O_n \Phi_n W_n^{-1} (W_n O_n^{-1}) = -W_n \Phi_n O_n^{-1} \quad (75)$$

And then substituting back into equation 74 yields:

$$\partial R'_{b,n} = (I + R'_{b,n}) W_n \Phi_n O_n^{-1}(D_n + jO_n^{-1})^{-1} W_n^{-1} \quad (76)$$

Substitute from equation 47 yields:

$$R'_{b,n} = W_n R_{b,n} W_n^{-1} \quad (77)$$

$$\partial R'_{b,n} = W_n(I + R_{b,n}) \Phi_n O_n^{-1}(D_n + jO_n^{-1})^{-1} W_n^{-1} \quad (78)$$

$$\partial R'_{b,n} = W_n(I + R_{b,n}) \Phi_n O_n^{-1} D_{l,n} W_n^{-1} \quad (79)$$

Where:

$$D_{l,n} = (D_n + O_n^{-1})^{-1}$$

It is noted that:

$$\partial e^{-jk_o S_n z} = W_n Y_{-,n} W_n^{-1} \quad (80)$$

Where:

$$Y_{\pm,n} = X_n \times K_{-,n} \text{ where } \{C \equiv A \times B : c_{mn} = a_{mn} b_{mn}\} \quad (81)$$

$$K_{\pm,n} : k_{\pm p,q} = \begin{cases} p \neq q : \pm \dfrac{(e^{\pm jk_o k_{zp} z} - e^{\pm jk_o k_{qj} z})}{(k_{zp} - k_{zq})} \\ p = q : \pm jk_o e^{\pm jk_o k_{zp} z} \end{cases} \quad (82)$$

Substituting equations 80 and 81 and $R'_{b,n} = W_n R_{b,n} W_n^{-1}$ into equation 70 yields:

$$\partial R'_{t,n} = W_n(Y_{-,n} R_{b,n} e^{-jk_o K_{z,n} z} + e^{-jk_o K_{z,n} z} W_n^{-1} \partial R'_{b,n} W_n \cdot e^{-jk_o K_{z,n} z} + e^{-jk_o K_{z,n} z} R_{b,n} Y_{-,n}) W_n^{-1} \quad (83)$$

Substituting equation 79 into equation 83 yields:

$$\partial R'_{t,n} = W_n(Y_{-,n} R_{b,n} e^{-jk_o K_{z,n} z} + e^{-jk_o K_{z,n} z}(I + R_{b,n}) \Phi_n O_n^{-1} D_{l,n} e^{-jk_o K_{z,n} z} + e^{-jk_o K_{z,n} z} R_{b,n} Y_{-,n}) W_n^{-1} \quad (84)$$

$$\partial R'_{t,n} = W_n(Y_{-,n} R_{b,n} e^{-jk_o K_{z,n} z} + e^{-jk_o K_{z,n} z} \Phi_n O_n^{-1} D_{l,n} e^{-jk_o K_{z,n} z} + e^{-jk_o K_{z,n} z} R_{b,n} \Phi_n O_n^{-1} D_{l,n} e^{-jk_o K_{z,n} z} + e^{-jk_o K_{z,n} z} R_{b,n} Y_{-,n}) W_n^{-1} \quad (85)$$

$$\partial R'_{t,n} = W_n(Y_{-,n} R_{b,n} e^{-jk_o K_{z,n} z} + e^{-jk_o K_{z,n} z} \Phi_n O_n^{-1} D_{l,n} e^{-jk_o K_{z,n} z} + e^{-jk_o K_{z,n} z} R_{b,n} (\Phi_n O_n^{-1} D_{l,n} e^{-jk_o K_{z,n} z} + Y_{-,n})) W_n^{-1} \quad (86)$$

$$\partial R'_{t,n} = W_n(Y_{-,n} R_{b,n} e^{-jk_o K_{z,n} z} + e^{-jk_o K_{z,n} z} \Theta_n + e^{-jk_o K_{z,n} z} R_{b,n}(\Theta_n + Y_{-,n})) W_n^{-1} \quad (87)$$

$$\partial R'_{t,n} = W_n A_n W_n^{-1} \quad (88)$$

Where:

$$\Theta_n = \Phi_n O_n^{-1} D_{l,n} e^{-jk_o K_{z,n} z} \quad (89)$$

Substituting equation 88 into equation 68 yields:

$$\partial Z_n = W_n(W_n^{-1} \partial R'_{t,n} W_n + Z'_n W_n^{-1} \partial R'_{t,n} W_n - Z'_n \Phi_n (I - R_{t,n}))(I - R_{t,n})^{-1} O_n^{-1} \quad (90)$$

$$\partial Z_n = W_n(A_n + Z'_n A_n - Z'_n \Phi_n (I - R_{t,n}))(I - R_{t,n})^{-1} O_n^{-1} \quad (91)$$

$$\partial Z_n = W_n((I + Z'_n) A_n (I - R_{t,n})^{-1} - Z'_n \Phi_n) O_n^{-1} \quad (92)$$

Rearranging these equations yields:

$$\partial Z_n = W_n((I + Z'_n) \Omega_n - Z'_n \Phi_n) O_n^{-1} = W_n(\Omega_n + Z'_n(\Omega_n - \Phi_n)) O_n^{-1} \quad (93)$$

Where:

$$\Omega_n = \Lambda_n (I - R_{t,n})^{-1} \quad (94)$$

PROPAGATION OF IMPEDANCE DERIVATIVE ABOVE GRATING LAYER: $F_{D(\ )}$

This process preferably begins with the expression for the impedance from equation 45, given below again:

$$Z_n = W_n Z'_n O_n^{-1} \qquad (95)$$

$$Z'_n = (I+R_{t,n})(I-R_{t,n})^{-1} \qquad (96)$$

$$R_{t,n} = e^{-jk_o K_{z,n} z} R_{b,n} e^{-jk_o K_{z,n} z} \qquad (97)$$

$$R_{b,n} = (D_{0,n} - O_n^{-1}) D_{1,n} \qquad (98)$$

$$D_{1,n} = (D_{0,n} + O_n^{-1})^{-1} \qquad (99)$$

$$D_{0,n} = W_n^{-1} Z_{n-1} \qquad (100)$$

$$O_n^{-1} = K_{z,n}^{-1} W_n^{-1} A_{\mu,n}^{-1} \qquad (101)$$

$$C_n = \lfloor K_{y,n} M_n^{-1} K_{y,n} - E_n \rfloor \qquad (102)$$

$F_n$ = Fourier series coefficient matrix (frequency independent)

$$A_{\mu,n} = (\mu_{line,n}^{-1} - \mu_{sp,n}^{-1}) F_n + (\mu_{sp,n}^{-1}) I \qquad (103)$$

$$S_n^2 = A_{\mu,n}^{-1} C_n \qquad (104)$$

Taking the derivative of equation 95 yields:

$$\partial Z_n = W_n \partial Z'_n O_n^{-1} \qquad (105)$$

Taking the derivative of equation 96 yields:

$$\partial Z'_n = \partial R_{t,n}(I-R_{t,n})^{-1} + (I+R_{t,n})(I-R_{t,n})^{-1} \partial R_{t,n}(I-R_{t,n})^{-1} \qquad (106)$$

$$\partial Z'_n = (I+Z'_n) \partial R_{t,n}(I-R_{t,n})^{-1} \qquad (107)$$

Taking the derivative of equation 47 yields:

$$\partial R_{t,n} = e^{-jk_o K_{z,n} z} \partial R_{b,n} e^{-jk_o K_{z,n} z} \qquad (108)$$

Taking the derivative of equation 48 yields:

$$\partial R_{b,n} = \partial D_{0,n} D_{1,n} + (D_{0,n} - O_n^{-1}) \partial D_{1,n} \qquad (109)$$

Taking the derivative of equation 49 yields:

$$\partial D_{1,n} = -D_{1,n} \partial D_{0,n} D_{1,n} \qquad (110)$$

Taking the derivative of equation 50 yields:

$$\partial D_{0,n} = W_n^{-1} \partial Z_{n-1} \qquad (111)$$

Substituting equation 110 into equation 111 finally yields:

$$\partial R_{b,n} = \partial D_{0,n} D_{1,n} - (D_{0,n} - O_n^{-1}) D_{1,n} \partial D_{0,n} D_{1,n} \qquad (112)$$

$$\partial R_{b,n} = (\partial D_{0,n} - R_{b,n} \partial D_{0,n}) D_{1,n} = (I - R_{b,n}) \partial D_{0,n} D_{1,n} \qquad (113)$$

VARIOUS DERIVATIVE DERIVATIONS

The proofs below are offered as support for the derivations provided above.

First proof: Prove:

$$\frac{\partial e^{\pm jk_o Sz}}{\partial p}\bigg|_{p \notin \{k_o, z\}} = W[X \times K_{\pm}]W^{-1}$$

Where:

$$X = W^{-1} \partial k_o SW, \{C \equiv A \times B : c_{mn} = a_{mn} b_{mn}\},$$

$$K_{\pm} : k_{\pm mn} = \begin{cases} \dfrac{(e^{\pm jk_o k_{zm} z} - e^{\pm jk_o k_{zn} z})}{(k_{zm} - k_{zn})} & m \neq n : \pm \\ \pm jk_o e^{jk_o k_{zn} z} z & m = n : \pm \end{cases}$$

Proof:

$$\partial e^{\pm jk_o Sz} = \pm j \int_0^z e^{\pm jk_o S(z-u)} \partial(k_o S) e^{\pm jk_o Su} du = \qquad \text{i)}$$

$$\pm j \int_0^z W e^{\pm jk_o K_z(z-u)} W^{-1} \partial(k_o S) W e^{\pm jk_o K_z u} W^{-1} du$$

(From Wilcox, 1967).
Define:
ii) $X = W^{-1} \partial(k_o S) W$
Hence:

$$\partial e^{\pm jk_o Sz} = \pm W \left[ j \int_0^z e^{\pm jk_o K_z(z-u)} X e^{\pm jk_o K_z u} du \right] W^{-1}$$

iii) Expand integrand of equation ii:

$$e^{\pm jk_o K_z(z-u)} X e^{\pm jk_o K_z u} =$$

$$k_o \begin{bmatrix} x_{00} e^{\pm jk_o k_{z0} z} e^{\pm jk_o(-k_{z0}+k_{z0})u} & \cdots & x_{0N} e^{\pm jk_o k_{z0} z} e^{\pm jk_o(-k_{z0}+k_{zN})u} \\ \vdots & x_{mn} e^{\pm jk_o k_{zm} z} e^{\pm jk_o(-k_{zm}+k_{zn})u} & \vdots \\ x_{N0} e^{\pm jk_o k_{zN} z} e^{\pm jk_o(-k_{zN}+k_{z0})u} & \cdots & x_{NN} e^{\pm jk_o k_{zN} z} e^{\pm jk_o(-k_{zN}+k_{zN})u} \end{bmatrix}$$

iv) (m, n)$^{th}$ element of $$m \neq n: \pm jk_o x_{mn} e^{\pm jk_o k_{zm} z} \int_0^z e^{\pm jk_o(-k_{zm}+k_{zn})u} du =$$

$$\pm x_{mn} e^{\pm jk_o k_{zm} z} \frac{e^{\pm jk_o(-k_{zm}+k_{zn})u}}{(-k_{zm}+k_{zn})} \bigg|_0^z \pm x_{mn} \frac{(e^{\pm jk_o k_{zm} z} - e^{\pm jk_o k_{zn} z})}{(k_{zm} - k_{zn})}$$

$$m \neq n: \pm jk_o x_{mn} e^{\pm jk_o k_{zm} z} \int_0^z du =$$

$$\pm jk_o x_{mn} e^{\pm jk_o k_{zm} z} u \big|_0^z = \pm jk_o x_{mm} e^{\pm jk_o k_{zn} z} z$$

v) Therefore, $$\pm j \int_0^z e^{jk_o K_z(z-u)} X e^{\pm jk_o K_z u} du = X \times K_\pm$$

where:

$$\{C \equiv A \times B : c_{mn} = a_{mn} b_{mn}\} \text{ and } K_\pm : k_{\pm mn} = \begin{cases} \frac{(e^{\pm jk_o k_{zm} z} - e^{\pm jk_o k_{zn} z})}{(k_{zm} - k_{zn})} \\ m \neq n: \pm \\ m = n: \pm jk_o e^{jk_o k_{zn} z} z \end{cases}$$

iv) Proof follows by substitution of equation v into equation ii.

Second proof: Prove:

$$\partial(S) = W\left[\frac{W^{-1} \partial S^2 W}{K_s}\right] W^{-1}$$

Where:

$$\left\{C \equiv \frac{A}{B} : c_{mn} = \frac{a_{mn}}{b_{mn}}\right\}$$

and $$K_s: k_{smn} = (k_{zm} + k_{zn})$$

Proof:
i) $\partial(S)^2 = \partial(S)S + S\partial(S)$
ii) $S = (WK_z W^{-1})$
iii) Substitute equation ii into equation i: $W^{-1} \partial S^2 W = \lfloor W^{-1} \partial(S)W \rfloor K_z + K_z \lfloor W^{-1} \partial(S)W \rfloor$ iv) Define $X = W^{-1} \partial(k_o S) W$ and expand equation iii:

$$W^{-1} \partial(S)^2 W =$$

$$XK_z + K_z X = \begin{bmatrix} x_{00}(k_{z0} + k_{z0}) & \cdots & x_{0N}(k_{z0} + k_{zN}) \\ \vdots & x_{mn}(k_{zm} + k_{zn}) & \vdots \\ x_{N0}(k_{zN} + k_{z0}) & \cdots & x_{NN}(k_{zN} + k_{zN}) \end{bmatrix}$$

v) From inspection of iv)

$$X = \left[\frac{W^{-1} \partial(k_o S)^2 W}{K_s}\right] \text{ where}$$

$$\left\{C \equiv \frac{A}{B} : c_{mn} = \frac{a_{mn}}{b_{mn}}\right\} \text{ and } K_s : k_{smn} = (k_{zm} + k_{zn})$$

Therefore, $$\partial S = WXW^{-1} = W\left[\frac{W^{-1} \partial S^2 W}{K_s}\right] W^{-1}$$

Third proof: Prove:

$$\partial e^{\pm jk_o Sz} = \pm jk_o \int_0^z e^{\pm jk_o S(z-u)} \partial S e^{\pm jk_o Su} du \quad \text{Wilcox(1967)}$$

Proof:
i) Factor $e^{\pm jk_o Sz}$ from integral in 1) and rewrite:

$$je^{\mp jk_o Sz} \partial e^{\pm jk_o Sz} = \pm jk_o \int_0^z e^{\mp jk_o Su} \partial S e^{\pm jk_o Su} du$$

ii) Fundamental Theorem of Calculus implies:

$$\frac{\partial}{\partial z}\left(e^{\mp jk_o Sz} \partial e^{\pm jk_o Sz}\right) = \pm jk_o e^{\mp jk_o Sz} \partial S e^{\pm jk_o Sz}$$

iii) Complete proof by showing that the right hand side of ii) is always equal to the left hand side:
iv) Expand right hand side and simplify:

$$\frac{\partial}{\partial z}\left(e^{\mp jk_o Sz} \partial e^{\pm jk_o Sz}\right) = \frac{\partial}{\partial z} e^{\mp jk_o Sz} \partial e^{\pm jk_o Sz} + e^{\mp jk_o Sz} \frac{\partial}{\partial z}(\partial e^{\pm jk_o Sz})$$

v) Exchange order of $$\frac{\partial}{\partial z}$$

and $\partial$ differentiation in last term:

$$\frac{\partial}{\partial z}\left(e^{\mp jk_o Sz} \partial e^{\pm jk_o Sz}\right) = \mp jk_o S e^{\mp jk_o Sz} \partial e^{\pm jk_o Sz} \pm jk_o e^{\mp jk_o Sz} \partial\left(Se^{\pm jk_o Sz}\right)$$

-continued $$\frac{\partial}{\partial z}\left(e^{\mp jk_oSz}\partial e^{\pm jk_oSz}\right) = \mp jk_oSe^{\mp k_oSz}\partial e^{\pm k_oSz} \pm jk_oe^{\mp k_oSz}S\partial e^{\pm k_oSz} \pm jk_oe^{\mp k_oS}\partial Se^{\pm k_oSz}$$

vi) From v), right hand side of ii) must always be equal to left hand side.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of determining actual properties of a film stack, the method comprising the steps of:
    directing an incident beam of light towards the film stack, such that the incident beam of light is reflected from the film stack as a reflected beam of light,
    measuring actual properties of the reflected beam of light,
    estimating properties of the film stack,
    solving a mathematical model of the film stack with the estimated properties of the film stack to yield theoretical properties of the reflected beam of light,
    comparing the theoretical properties of the reflected beam of light to the actual properties of the reflected beam of light to yield a cost function,
    iteratively adjusting the estimated properties of the film stack and solving the mathematical model until the cost function is within a desired tolerance, and
    reporting the estimated properties of the film stack as the actual properties of the film stack,
    where a method based on analytical derivatives, and not numerically computed derivatives, of solutions to Maxwell's equations that are at least partially expressible as complex exponential matrices is used to iteratively adjust the estimated properties of the film stack.

2. The method of claim 1, wherein the method is implemented in one of an ellipsometer and a reflectometer.

3. The method of claim 1, wherein the film stack comprises layers of more than one material.

4. The method of claim 1, wherein the film stack comprises more than one layer.

5. The method of claim 1, wherein the film stack includes a patterned layer.

6. The method of claim 1, wherein the actual properties of the film stack include at least one of layer thickness, refractive index, roughness, pattern geometry, material properties, offset between pattern layers, substrate properties, and tool model parameters.

7. The method of claim 1, wherein the mathematical model is a reflectance model that is derived using rigorous coupled wave analysis.

8. The method of claim 1, wherein adjustments to the estimated film stack properties to reduce the cost function are given by:

$$\frac{\partial C(R_{meas}(\lambda_m), R_{theory}(\lambda_m, P))}{\partial P_n} = \sum_{m=0}^{M}\left(\frac{\partial C}{\partial R_{theory}}\right)\left(\frac{\partial R_{theory}(\lambda_m, P)}{\partial P_n}\right) = 0$$

where C is the cost function, $R_{theory}$ is a theoretical reflectance, $R_{meas}$ is a measured reflectance, $P_n$ is a variable of the film stack properties, $\lambda_m$ is an $m^{th}$ wavelength, m is an integer index, M is a total number of wavelength values, and $\sigma_m$ is a measurement uncertainty at $\lambda_m$.

9. The method of claim 1, wherein the estimated properties of the film stack are derived exactly and in closed form.

10. The method of claim 1, wherein the mathematical model of the film stack contains at least one film that possesses a patterned layer that varies periodically in one spatial direction.

11. The method of claim 1, wherein the mathematical model of the film stack contains at least one film that possesses a patterned layer that varies periodically in two spatial direction.

12. The method of claim 1, wherein the solutions to Maxwell's equations used to iteratively adjust the estimated properties of the film stack are expressed in eigenvalues and non-diagonal eigenvector matrices.

13. A method of determining with an ellipsometer actual properties of a film stack of more than one layer and more than one material and including a patterned layer, the actual properties including at least one of layer thickness and layer refractive index, the method comprising the steps of:
    directing an incident beam of light towards the film stack, such that the incident beam of light is reflected from the film stack as a reflected beam of light,
    measuring actual properties of the reflected beam of light,
    estimating properties of the film stack,
    solving a mathematical model of the film stack with the estimated properties of the film stack to yield theoretical properties of the reflected beam of light, wherein the mathematical model is a reflectance model that is derived using rigorous coupled wave analysis,
    comparing the theoretical properties of the reflected beam of light to the actual properties of the reflected beam of light to yield a cost function,
    iteratively adjusting the estimated properties of the film stack and solving the mathematical model until the cost function is within a desired tolerance, and
    reporting the estimated properties of the film stack as the actual properties of the film stack,
    where a method based on analytical derivatives, and not numerically computed derivatives, of solutions to Maxwell's equations that are at least partially expressible as complex exponential matrices is used to iteratively adjust the estimated properties of the film stack.

14. The method of claim 13, wherein adjustments to the estimated film stack properties to reduce the cost function are given by:

$$\frac{\partial C(R_{meas}(\lambda_m), R_{theory}(\lambda_m, P))}{\partial P_n} = \sum_{m=0}^{M}\left(\frac{\partial C}{\partial R_{theory}}\right)\left(\frac{\partial R_{theory}(\lambda_m, P)}{\partial P_n}\right) = 0$$

where C is the cost function, $R_{theory}$ is a theoretical reflectance, $R_{meas}$ is a measured reflectance, $P_n$ is a variable of the film stack properties, $\lambda_m$ is an $m^{th}$ wavelength, m is an integer index, M is a total number of wavelength values, and $\sigma_m$ is a measurement uncertainty at $\lambda_m$.

15. The method of claim 13, wherein the mathematical model of the film stack contains at least one film that possesses a patterned layer that varies periodically in one spatial direction.

16. The method of claim 13, wherein the mathematical model of the film stack contains at least one film that possesses a patterned layer that varies periodically in two spatial direction.

17. The method of claim 13, wherein the solutions to Maxwell's equations used to iteratively adjust the estimated properties of the film stack are expressed in eigenvalues and non-diagonal eigenvector matrices.

18. A method of determining with an ellipsometer actual properties of a film stack of more than one layer and more than one material and including a patterned layer, the actual properties including at least one of layer thickness and layer refractive index, the method comprising the steps of:

directing an incident beam of light towards the film stack, such that the incident beam of light is reflected from the film stack as a reflected beam of light, measuring actual properties of the reflected beam of light, estimating properties of the film stack, solving a mathematical model of the film stack with the estimated properties of the film stack to yield theoretical properties of the reflected beam of light, wherein the mathematical model is a reflectance model that is derived using rigorous coupled wave analysis, comparing the theoretical properties of the reflected beam of light to the actual properties of the reflected beam of light to yield a cost function, iteratively adjusting the estimated properties of the film stack and solving the mathematical model until the cost function is within a desired tolerance, wherein adjustments to the estimated film stack properties to reduce the cost function are given by:

$$\frac{\partial C(R_{meas}(\lambda_m), R_{theory}(\lambda_m, P))}{\partial P_n} = \sum_{m=0}^{M} \left(\frac{\partial C}{\partial R_{theory}}\right)\left(\frac{\partial R_{theory}(\lambda_m, P)}{\partial P_n}\right) = 0$$

where C is the cost function, $R_{theory}$ is a theoretical reflectance, $R_{meas}$ is a measured reflectance, $P_n$ is a variable of the film stack properties, $\lambda_m$ is an $m^{th}$ wavelength, m is an integer index, M is a total number of wavelength values, and $\sigma_m$ is a measurement uncertainty at $\lambda_m$, and reporting the estimated properties of the film stack as the actual properties of the film stack, where a method based on analytical derivatives, and not numerically computed derivatives, of solutions to Maxwell's equations that are at least partially expressible as complex exponential matrices is used to iteratively adjust the estimated properties of the film stack.

19. The method of claim 18, wherein the mathematical model of the film stack contains at least one film that possesses a patterned layer that varies periodically in one spatial direction.

20. The method of claim 18, wherein the solutions to Maxwell's equations used to iteratively adjust the estimated properties of the film stack are expressed in eigenvalues and non-diagonal eigenvector matrices.

* * * * *